(12) United States Patent
Jimenez et al.

(10) Patent No.: US 9,433,587 B2
(45) Date of Patent: *Sep. 6, 2016

(54) ACNE SOLUTION

(71) Applicant: Envy Medical, Inc., Westlake Village, CA (US)

(72) Inventors: Felipe Jimenez, Rialto, CA (US); Lyndon Garcines, Fountain Valley, CA (US); Susan Goldsberry, Huntington Beach, CA (US); Senad Ibrulj, Santa Ana, CA (US)

(73) Assignee: Envy Medical, Inc., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,718

(22) Filed: Apr. 21, 2015

(65) Prior Publication Data

US 2015/0238440 A1 Aug. 27, 2015

Related U.S. Application Data

(63) Continuation-in-part of application No. 13/783,066, filed on Mar. 1, 2013, now Pat. No. 9,295,723.

(60) Provisional application No. 61/982,229, filed on Apr. 21, 2014.

(51) Int. Cl.
*A61K 31/05* (2006.01)
*A61K 36/63* (2006.01)
*A61K 36/535* (2006.01)
*A61K 36/487* (2006.01)
*A61K 31/60* (2006.01)
*A61K 31/045* (2006.01)
*A61K 9/08* (2006.01)
*A61K 45/06* (2006.01)
*A61K 47/38* (2006.01)

(52) U.S. Cl.
CPC ............... *A61K 31/05* (2013.01); *A61K 9/08* (2013.01); *A61K 31/045* (2013.01); *A61K 31/60* (2013.01); *A61K 36/487* (2013.01); *A61K 36/535* (2013.01); *A61K 36/63* (2013.01); *A61K 45/06* (2013.01); *A61K 47/38* (2013.01)

(58) Field of Classification Search
None
See application file for complete search history.

(56) References Cited

U.S. PATENT DOCUMENTS

| 2008/0069898 A1 | 3/2008 | Smith et al. |
| 2009/0137534 A1 | 5/2009 | Chaudhuri |
| 2010/0040696 A1 | 2/2010 | Sente et al. |
| 2012/0201769 A1 | 8/2012 | Hong et al. |

FOREIGN PATENT DOCUMENTS

WO 2014134620 9/2014

OTHER PUBLICATIONS

International Search Report and Written Opinion, PCT Application PCT/US2015/026958, Aug. 5, 2015, 15 pages.

*Primary Examiner* — Ernst V Arnold
*Assistant Examiner* — Kyung Sook Chang
(74) *Attorney, Agent, or Firm* — Aka Chan LLP

(57) ABSTRACT

A composition for the treatment of acne includes hydrolyzed *psoralea corylifolia*, containing a component bakuchiol, is solubilized in a water-based solution. The composition is for topical application to the skin. In various implementations, the composition is a water-based acne gel or a water-based cleanser. In a specific implementation, a composition includes Bakutrol™, which includes bakuchiol, and bisabolol. The composition can include a polysorbate surfactant. In implementations, these ingredients are combined with other active ingredients, including for example, salicylic acid, benzoyl peroxide, tretinoin, retinol, tazarotene, or an antibiotic, or a combination of these. A process of preparation of the composition allows for the stabilization of Bakutrol in solution.

7 Claims, No Drawings

ACNE SOLUTION

CROSS-REFERENCE TO RELATED APPLICATIONS

This application claims the benefit of U.S. patent application Ser. No. 61/982,229, filed Apr. 21, 2014 and is a continuation-in-part of U.S. patent application Ser. No. 13/783,066, filed Mar. 1, 2013. These applications are incorporated by reference along with all other references cited in this application.

BACKGROUND OF THE INVENTION

The invention relates to the field of skincare compositions and more specifically to compositions for treating acne vulgaris.

Acne vulgaris (acne) is a chronic inflammatory condition of the pilosebaceous units of the skin, which is particularly prevalent in adolescents. The condition generally causes the formation, on the skin, of comedones, red papules, pustules and sometimes cysts. This is unsightly and furthermore, if untreated, acne can lead to scarring of the skin. The major causes of acne are thought to be an increase in sebum production, an increased presence of *proprionibacterium acnes* (*P. acne*), blockage of the pilosebaceus duct and the production of inflammation.

Typical treatments for acne include therapies containing benzoyl peroxide, retinoids or a combination of an antibiotic and benzoyl peroxide. However, these therapies are harsh on the skin and can cause excessive dryness, redness, irritation, and peeling. These therapies can take between 3 to 6 weeks to reduce inflammatory acne lesions by fifty percent. The amount of time its takes for typical acne treatment products to work and the tolerability issues they present, cause users to be noncompliant in using these products as prescribed; experience little to no reduction in acne; and be less likely to re-purchase the acne products.

There is a continuing demand for acne treatment therapies that are more effective and potent, and easy to use, while minimizing harsh side effects on the skin. Therefore, there is a need for improved treatment products for acne.

BRIEF SUMMARY OF THE INVENTION

A composition and process of preparation of a compound is for the treatment of acne. The compound is for topical application to the skin. Specifically, the composition includes Bakutrol™, containing the ingredient bakuchiol, that is solubilized in a water-based solution.

In a specific implementation, a composition includes hydrolyzed *psoralea corylifolia* containing bakuchiol as a primary component (or Bakutrol), and bisabolol. The composition can include a preservative, a surfactant, an emollient, or a combination of these. In a specific implementation, Bakutrol and bisabolol RAC are combined with polysorbate 20 as the preservative. In implementations, these ingredients are combined with other active ingredients, including for example, salicylic acid or benzoyl peroxide (BPO). Combining active ingredients (e.g., BPO) with bakuchiol and bisabolol can render the active ingredients less irritating to the skin because both bakuchiol and bisabolol possess anti-inflammatory properties.

In a specific implementation, a composition includes Bakutrol, bisabolol, polysorbate 20, and other ingredients: salicylic acid, *olea europaea* (olive) fruit extract, *perilla ocymoides* leaf extract (e.g., shiso extract powder), sodium PCA, hydroxyethylcellulose, disodium EDTA, gluconolactone, lactic acid, sodium benzoate, dextrin, water, glycolic acid, sodium hydroxide, and butylene glycol. In other implementations, the composition can include Bakutrol and any one or more of the ingredients, in any combination.

A method of preparation is for a water-based acne gel composition. The preparation solubilizes Bakutrol which allows it to be effectively absorbed by the skin, and allows it to be stable in the gel. The gel is effective in reducing inflammatory acne lesions by 50 percent in as few as about 7 days with a 90 percent reduction achieved in about 14 days. Unlike typical prescription and over-the-counter acne treatments, the gel does not cause collateral damage to the skin, including dry skin, skin irritation, redness, and peeling.

In an implementation, a method of preparing an aqueous mixture includes: mixing deionized water and hydroxyethylcellulose to obtain a first mixture; applying heat to the first mixture until the first mixture reaches about 75 degrees Celsius; adding disodium ethylenediaminetetraacetic acid (EDTA) and sodium pyrrolidone carboxylic acid (PCA) to the first mixture and mixing to obtain a second mixture; allowing the second mixture to cool to from about 60 to 65 degrees Celsius; mixing butylene glycol and salicylic acid to obtain a third mixture; applying heat to the third mixture until the third mixture reaches about 65 degrees Celsius; mixing the third mixture and second mixture together to obtain a fourth mixture; allowing the fourth mixture to cool to from about 55 to 60 degrees Celsius; adding glycolic acid and lactic acid to the fourth mixture and mixing to obtain a fifth mixture; allowing the fifth mixture to cool to from about 50 to 55 degrees Celsius; mixing deionized water and sodium hydroxide to obtain a sixth mixture; mixing the sixth mixture and the fifth mixture together to obtain a seventh mixture; and allowing the seventh mixture to cool to from about 45 to 50 degrees Celsius.

The method further includes: mixing deionized water and *perilla ocymoides* leaf extract to obtain an eighth mixture; mixing the eighth mixture and the seventh mixture to obtain a ninth mixture; mixing deionized water and *olea europaea* fruit extract to obtain a tenth mixture; mixing the tenth mixture and ninth mixture to obtain an eleventh mixture; allowing the eleventh mixture to cool to from about 40 to 45 degrees Celsius; adding sodium benzoate to the eleventh mixture and mixing to obtain a twelfth mixture; and solubilizing an unsolubilized hydrolyzed *psoralea corylifolia* extract to obtain a solubilized hydrolyzed *psoralea corylifolia* extract including mixing the unsolubilized hydrolyzed *psoralea corylifolia* extract, bisabolol, and polysorbate 20 to obtain a thirteenth mixture, and adding the thirteenth mixture to the twelfth mixture at a temperature of less than about 40 degrees Celsius to obtain a fourteenth mixture, where the fourteenth mixture includes the solubilized hydrolyzed *psoralea corylifolia* extract;

The method further includes: mixing encapsulated retinol to the fourteenth mixture to obtain a fifteenth mixture; allowing the fifteenth mixture to cool to about 35 degrees Celsius; and obtaining an aqueous mixture that is a combination of the twelfth and thirteenth mixtures and retinol, where the aqueous mixture includes an oil-free, water-based, anti-acne gel.

In various implementations, the method can further include adding benzoyl peroxide to the polysorbate 20, bisabolol, and hydrolyzed *psoralea corylifolia* extract of the thirteenth mixture. The aqueous mixture can include at least one of a retinoid or an antibiotic. The hydrolyzed *psoralea corylifolia* extract can include bakuchiol. The aqueous mixture does not include an alcohol or oil constituent.

Further, the solubilizing an unsolubilized hydrolyzed *psoralea corylifolia* at a temperature of less than about 40 degrees Celsius results in a particle size of bakuchiol in the hydrolyzed *psoralea corylifolia* extract that is of a sufficiently small size to penetrate skin pores into sebaceous follicles where the hydrolyzed *psoralea corylifolia* extract can exert its antimicrobial and anti-inflammatory properties.

In another implementation, a mixture includes: hydrolyzed *psoralea corylifolia* extract; bisabolol, where the hydrolyzed *psoralea corylifolia* extract and bisabolol are solubulized together; retinol; and a surfactant, where the mixture is aqueous solution without oil and without an alcohol.

In various implementations, the mixture can further include at least one of benzoyl peroxide, tretinoin, tazarotene, or an antibiotic. The antibiotic can be clindamycin or erythromycin. A ratio of hydrolyzed *psoralea corylifolia* extract to bisabolol is about 10:1 or less.

The retinol can be an encapsulated retinol. Alternatively, the retinol can be an unencapsulated retinol; then the hydrolyzed *psoralea corylifolia* extract, bisabolol, and unencapsulated retinol are solubulized together.

In a cleanser formulation, the surfactant can include cocamidopropyl betaine having a weight-weight percentage greater than 10 percent. The surfactant can include decyl glucoside having a weight-weight percentage greater than 20 percent. The surfactant can include cocamidopropyl betaine having a weight-weight percentage greater than 10 percent and decyl glucoside having a weight-weight percentage greater than 20 percent.

In a gel, lotion, or similar formulation (not cleanser), the surfactant can include polysorbate 20 having a weight-weight percentage less than 3 percent. Further, the surfactant can include polysorbate 20 having a weight-weight percentage less than 3 percent, and without cocamidopropyl betaine or decyl glucoside, such as in the cleanser formulation.

Other objects, features, and advantages of the present invention will become apparent upon consideration of the following detailed description and the accompanying drawings, in which like reference designations represent like features throughout the figures.

DETAILED DESCRIPTION OF THE INVENTION

Acne is a common skin condition, characterized by areas of skin with seborrhea (scaly red skin), comedones (blackheads and whiteheads), papules (pinheads), pustules (pimples), nodules (large papules) and possibly scarring.

Approximately 650 million people worldwide, or about 9.4 percent of the world population, experience some degree of acne. In the United States alone, acne affects about 40 to 50 million people annually. Research has shown that about 85 percent of young people between the ages of 12 and 24 years have acne, and while it is most common in teenagers, acne affects 8 percent of adults aged 25 to 34 years and 3 percent of adults aged 35 to 44 years.

Modern societies place a great emphasis on physical appearance. Although acne is not a life-threatening condition, it has significant physical and psychological ramifications such as permanent scarring, poor self-image and self-esteem, social phobia, social dysfunction, depression, anxiety, suicide, and overall reduced quality of life. Therefore, acne should be regarded as a serious medical disorder.

The available topical agents for the treatment of acne typically include benzoyl peroxide, retinoids, antibiotics, antiseborrheic medications, antiandrogen medications, hormonal treatments, salicylic acid, alpha hydroxy acid, and a combination of these. The therapeutic success in acne of these treatments is highly dependent on a regular application of the topical agents over a prolonged period of time. However, disadvantages associated with these commonly used topical agents considerably affect patient compliance and obstruct the treatment. These agents can cause undesirable side effects such as excessive dryness, redness, irritation, and peeling. In addition, the use of antibiotics has limitations due to development of resistance by bacteria. The use of retinoids has also been linked to causing developmental malformations.

These agents can take long periods of time to work. Research has shown that even effective prescription and over-the-counter acne treatment products can take up to between 3 to 6 weeks to reduce inflammatory acne lesions by about 50 percent. These and other disadvantages can cause users to be noncompliant in using acne products as prescribed.

Bakutrol™ is an antimicrobial and anti-inflammatory agent that has been shown to help reduce the bacterial activity, inflammation, and scarring seen in acne. Bakutrol is a trademark of Unigen, Inc. Any trademarks listed in this patent application are the property of their respective owners. Bakutrol is a natural, botanical agent. It contains bakuchiol, a natural phenol isolated from the seeds of *Psoralea corylifolia* or *Psoralea glandulosa*, a tree native to China known for its uses in traditional Chinese medicine.

Bakuchiol has a natural ability to fight inflammation, by controlling leukocytic functions at the site of the inflammation. In clinical studies, Bakutrol reduced both inflammatory and noninflammatory acne lesions without the adverse side effects often found with harsh chemicals. Bakuchiol also possesses protective antioxidant characteristics due to its scavenging activity against oxidative damage to lipids and proteins. Additionally, Bakutrol significantly reduces scarring or post-inflammatory hyperpigmentation (PIH), the dark spots left behind long after the acne lesion has healed. Unlike traditional acne treatments, Bakutrol has been clinically proven to reduce PIH. In some studies, bakuchiol has been shown to be more potent at treating acne than benzoyl peroxide.

Research on bakuchiol demonstrates its ability to inhibit both the growth of acne-causing bacteria and the COX/LOX inflammatory pathways. Bakuchiol has also been shown to regulate sebum production. A pilot study on subjects with a diagnosis of facial acne vulgaris showed significant reductions in inflammatory (papules, cysts) and noninflammatory (blackheads) lesions. Forty-five percent of these study subjects also experienced partial or total clearing of acne-related postinflammatory hyperpigmentation (PIH) which can follow acne vulgaris and results in skin melanosis (dark pigmentation).

Hydrolyzed *psoralea corylifolia*, containing bakuchiol, has hydrophobic properties and is naturally insoluble in water. The hydrolysis of *psoralea corylifolia* extracts the component bakuchiol, which is contained in Bakutrol. It is very difficult to incorporate bakuchiol into a water-based preparation (e.g., water-based gel preparation) for topical use since bakuchiol is insoluble. Some prescription and over-the-counter acne products contain suspended particles of bakuchiol that are very large and cannot penetrate into sebaceous follicles (pores). The skin cannot absorb these products even when excess amounts of bakuchiol are present. These products are therefore, ineffective at delivering bakuchiol to the dermal tissue. Furthermore, due to bakuchiol's inability to solubilize in water, bakuchiol can become unstable in aqueous solutions.

A novel technology includes a unique formulation and preparation of a solution in which bakuchiol (Bakutrol) is solubilized, without the use of alcohol. When Bakutrol is solubilized, it can be effectively delivered into the sebaceous follicles (pores) with ingredients such as bisabolol where these ingredients, with salicylic acid, can promote rapid clinical results. Solubilized Bakutrol can be easily absorbed by the skin. Hence, the skin treatment properties of Bakutrol are significantly enhanced when it is solubilized.

To solubilize bakuchiol, which has hydrophobic properties, bakuchiol (from hydrolyzed *psoralea corylifolia* extract) is premixed with another hydrophobic ingredient. In a specific implementation, bakuchiol and the other hydrophobic ingredient are premixed at room temperature in a mixing vessel. The hydrophobic molecules of the ingredients can be mixed together without precipitation because hydrophobic molecules form stable hydrophobic interactions with one another. The mixture containing the solubilized bakuchiol can then be emulsified into a solution to obtain a skincare product. This method yields a stable formula whereby the bakuchiol is completely solubilized.

Research has shown that there is a synergistic effect in solubilizing bakuchiol (e.g., Bakutrol), rather than an additive effect, when combinations of the ingredients listed above are combined. In a mixture of ingredients, each ingredient works through a specific mechanism of action, and has an individual effect when combined with bakuchiol. An additive effect of the mixture is the same as the sum of the individual effects of each ingredient. In contrast, a synergistic effect of a mixture of substances is greater than the sum of the individual effects. For example, compounds A and B each has a solubility rate of 10 percent when used individually. However in combination, the actual combined solubility rate is 30 percent, rather than an anticipated additive effect of 20 percent, resulting in an enhancement of 10 percent. The combinations of ingredients, such as those presented above, have been shown to produce this synergistic effect. In combination, the solubility of bakuchiol is amplified. Consequently, the combination of ingredients can be effective in solubilizing and stabilizing bakuchiol, while optimizing the benefits of bakuchiol, and can increase the duration of time of stability of the bakuchiol in a solution (e.g., water-based gel solution).

In these implementations, bakuchiol can be solubilized to allow for a composition with enhanced acne treatment properties. As discussed above, when bakuchiol is solubilized, it can be effectively absorbed into the skin to treat the skin. Research has shown that in a specific implementation of the composition, the product (a water-based acne gel), after applied to users' acne areas over several weeks, reduced inflammatory acne lesions by 50 percent in about 7 days with a 90 percent reduction achieved in 14 days. The product was also seen to work about three times faster than typical prescription and over-the-counter acne products. The results showed that the product does not cause collateral damage to the skin, including dry skin, skin irritation, redness, and peeling.

In these implementations, bakuchiol is stable in the product, while retaining its acne treatment properties. Some accelerated stability studies show that the product is stable for about one month to about 3 months at 25 degrees Celsius, 4 degrees Celsius, and 40 degrees Celsius, with no separation or precipitation. This correlates to about an 8 month to about 24 months shelf life.

In various implementations, bakuchiol is solubilized using another hydrophobic ingredient, bisabolol. Bisabolol is the main active ingredient of the medical plant chamomile (*matricaria chamomilla*). Bisabolol protects and heals the skin from the effects of daily stress. It is a naturally occurring active ingredient that accelerates the healing process of skin. Research has shown that it contains anti-inflammatory properties.

Both bisabolol and bakuchiol have hydrophobic properties and are generally insoluble in water and other aqueous solutions. They are typically formulated into the oil phase of emulsions. However, the bakuchiol (from hydrolyzed *psoralea corylifolia* extract) will not stay in solution and precipitates out when added to the oil phase of an emulsion. This prevents the hydrolyzed *psoralea corylifolia* extract from being absorbed by the pores of the skin.

Thus, to solubilize bakuchiol, bakuchiol is premixed with bisabolol. Bakuchiol and bisabolol can be mixed together without precipitation because hydrophobic molecules form hydrophobic interactions with one another. The mixture, containing the solubilized bakuchiol, can then be emulsified into an emulsion. This method yields a stable formula whereby the bakuchiol is completely solubilized.

In a specific implementation, a composition includes hydrolyzed *psoralea corylifolia*, containing bakuchiol as its primary component (or Bakutrol) and bisabolol. The composition can include a polysorbate surfactant, which is a stable and relatively nontoxic agent that allows it to be used as a detergent and emulsifier in a number of domestic, scientific, and pharmacological applications. In pharmaceutical applications, it is used to stabilize emulsions and suspensions. In a specific implementation, bakuchiol and bisabolol RAC are combined with polysorbate 20 as the emulsifier.

In a specific implementation, a composition includes bakuchiol (or hydrolyzed *psoralea corylifoli* extract), bisabolol, polysorbate 20, and other ingredients: salicylic acid, *olea europaea* (olive) fruit extract, *perilla ocymoides* leaf extract (e.g., shiso extract powder), sodium PCA, hydroxyethylcellulose, disodium EDTA, gluconolactone, lactic acid, sodium benzoate, dextrin, water, glycolic acid, sodium hydroxide, butylene glycol, or any combination of these. In other implementations, the composition can include bakuchiol and any one or more of the ingredients, in any combination. Other ingredients (and their equivalents) can be substituted for or replace any of the one or more of the listed ingredients. For example, polysorbate 20 can be replaced by caprylyl glycol, ethylhexylglycerin, or PPG-2 isoceteth-20 acetate.

In a specific implementation, a mixture includes hydrolyzed *psoralea corylifolia* extract (e.g., bakuchiol), bisabolol, salicylic acid, and a surfactant, in an aqueous solution. In various implementations, this mixture can be combined with benzoyl peroxide, tretinoin, retinol, tazarotene, or an antibiotic, or a combination of these. Some examples of antibiotics include clindamycin or erythromycin. The mixture can include any combination of antibiotics. In various implementations, polysorbate 20 can be used to emulsify these ingredients into a finished formulation.

In specific implementations, a mixture includes bakutrol, bisabolol, polysorbate 20, and at least one of the lipophilic compounds: anti-acne compounds (e.g. benzoyl peroxide, or salicylic acid, or others), retinoids (e.g., retinol, tretinoin, tazarotene, or others), antibiotics (e.g., erythromycin, clindamycin, or others), or any combination of these.

A specific implementation of mixtures with one varying ingredient can have different relative degrees of efficacies.

For example, a specific implementation of mixtures can include bakutrol, bisabolol, polysorbate 20 and one of the following: tretinoin, tazarotene, retinol, or benzoyl peroxide. The relative degrees of efficacies of the above mixtures can be arranged in the following manner (from most efficacious mixture to least efficacious): (1) tretinoin, (2) tazarotene, (3) retinol, and (4) benzoyl peroxide.

Another specific implementation of mixtures can have a different arrangement of relative degrees of efficacy. For example, another implementation of mixtures can include bakutrol, bisabolol, polysorbate 20 and two of the following: tretinoin, tazarotene, retinol, or benzoyl peroxide. A specific implementation can include bakutrol, bisabolol, polysorbate 20, retinol (third most efficacious in another implementation), and benzoyl peroxide (least efficacious in another implementation). This mixture can be more efficacious than a mixture including bakutrol, bisabolol, polysorbate 20, tretinoin (most efficacious in another implementation), and tazarotene (second most efficacious in another implementation).

The relative degrees of efficacies can change because a combination of lipophilic compounds can have a synergistic effect on efficacy. For example, a mixture including bakutrol, bisabolol, polysorbate 20, retinol, and benzoyl peroxide can be more efficacious than the combined additive efficacy of (1) a mixture including bakutrol, bisabolol, polysorbate 20, and retinol, and (2) a mixture including bakutrol, bisabolol, polysorbate 20, and benzoyl peroxide.

Further, one combination of lipophilic compounds can have a stronger synergistic effect on efficacy than a second combination of lipophilic compounds. For example, a mixture including bakutrol, bisabolol, polysorbate 20, retinol, and benzoyl peroxide can have a stronger synergistic effect on efficacy and be more efficacious than a mixture including bakutrol, bisabolol, polysorbate 20, tretinoin, and tazarotene, which can have a weaker synergistic effect on efficacy.

Tetracycline is an antibiotic sometimes used in the treatment of acne vulgaris and is usually administered orally. Tetracycline can be used in topical form to treat acne vulgaris, but generally has poor absorption into the skin. So, other antibiotics are typically better suited for topical formulations than tetracycline.

Generally, hydrophobic ingredients such as benzoyl peroxide, tretinoin, retinol, tazarotene and other hydrophobic ingredients are generally insoluble in water and other aqueous solutions. Thus, to solubilize these ingredients, they are combined with other hydrophobic ingredients such as bakuchiol or bisabolol, or both. More specifically, bakuchiol, which has a similar hydrophobicity value (octanol-water partition coefficient) to that of tretinoin, retinol, and tazarotene, and a greater hydrophobicity value than that of benzoyl peroxide, can be used to solubilize these ingredients. Similarly, bisabolol, which is similar in structure and hydrophobicity to ingredients such as retinoids and retinol, can also be used to solubilize retinoids such as tretinoin and retinol. This is based on the concept that polar (i.e., hydrophilic) substances can dissolve other polar substances, and nonpolar (i.e., hydrophobic) substances dissolve nonpolar substances, while nonpolar substances do not dissolve in polar substances.

In a specific implementation, a mixture of bakuchiol, bakutrol, and polysorbate 20, along with other ingredients such as salicylic acid, can be used to solubilize other similar hydrophobic anti-acne ingredients such as tretinoin, retinol, tazarotene and benzoyl peroxide without the use of alcohol or other solvents that may irritate skin. This method yields a stable formula in which the hydrophobic ingredients are solubilized.

A specific implementation of the mixture described in this patent is an aqueous solution. An aqueous solution is used for an acne formulation because it is gentler, and irritates the skin less than a nonaqueous solution. Nonaqueous solution can irritate the skin and may cause inflammation, which can make the acne condition to worsen (e.g., cause acne breakouts, make the skin more sensitive, or enlarge the affected area).

However, in various implementations, a mixture as described in this patent can include a nonaqueous solvent. These nonaqueous solvents can be added in trace or as a relatively small percentage (or greater) of the total mixture. Such nonaqueous solvents can help in the dissolution of some of the components of the mixture, improve stability of the mixture, used to adjust the pH balance or polarity of the solution, or other. Further a mixture with nonaqueous solvents can be used for specific acne conditions or acne in particular areas of the body that do not respond or adhere as well to aqueous solvents (e.g., near sweat glands where the mixture would get washed or flushed away quickly).

Therefore, in various implementations, a mixture can include one or more solvents, other than water, including a polar solvent or nonpolar solvent, or a combination of these. Some examples of solvents include alcohol, isododecane, octyldodecanol, heptane, pentane, or benzyl benzoate. The mixture can include any combination of solvents with or without water.

In another implementation, the hydrolyzed *psoralea corylifolia* extract (e.g., bakuchiol) of the mixture can be substituted with benzoyl peroxide, tretinoin, retinol, tazarotene, or an antibiotic, or a combination of these.

In another implementation, the bisabolol of the mixture can be substituted with benzoyl peroxide, tretinoin, retinol, tazarotene, or an antibiotic, or a combination of these.

In a specific implementation, a composition includes bakuchiol and bisabolol in an aqueous solution. In other implementations, the composition can be combined with other ingredients such as one or more anti-acne compounds (e.g., salicylic acid, benzoyl peroxide, and many others), one or more retinoids (e.g., retinol, tretinoin, tazarotene, and many others), one or more antibiotics (e.g., erythromycin, clindamycin, and many others), one or more surfactants, or one or more emollients, or any combination of these.

Salicylic acid is a keratolytic agent with anti-inflammatory properties. Benzoyl peroxide is a keratolytic agent with antibacterial properties. Because salicylic acid and benzoyl peroxide treat acne in different ways (anti-inflammation versus antibacterial), salicylic acid and benzoyl peroxide can be combined together to treat acne in multiple ways and result in a more effective anti-acne product. Because salicylic acid and benzoyl peroxide are both keratolytic agents, salicylic acid and benzoyl peroxide can also substitute for each other in a mixture.

However, a combination of salicylic acid and benzoyl peroxide can be too irritating to the skin. The U.S. Food and Drug Administration (FDA) has outlined the types of anti-acne ingredients that are permitted to be in a single over-the-counter formula or product. The limitations outlined by the FDA do not pertain to combinations for prescription drug ingredients.

The FDA has permitted certain types of single active ingredient anti-acne products to be sold over the counter. For example, an over-the-counter product can have benzoyl peroxide, as the single active ingredient, in concentrations of 2.5 percent to 10 percent. Or a product can have salicylic acid, as the single active ingredient, in concentrations of 0.5 percent to 2 percent. Or a product can have sulfur, as the single active ingredient, in concentrations of 3 percent to 10 percent.

The FDA also permits certain combinations of active ingredients in anti-acne products sold over the counter. For example, an over-the-counter anti-acne product can have a combination of resorcinol in a concentration of 2 percent and sulfur in concentrations of 3 percent to 8 percent. Or a product can have a combination of resorcinol monoacetate in a concentration of 3 percent and sulfur in concentrations of 3 percent to 8 percent.

Therefore, to prevent excess irritation, some implementations of the mixture include salicylic acid or the like, without benzoyl peroxide or the like.

For example, in a specific implementation, the composition includes bakuchiol and bisabolol and at least one of benzoyl peroxide, salicylic acid, tretinoin, retinol, tazarotene, or an antibiotic. In other implementations, any one of the ingredients can be omitted or replaced with another ingredient such as an anti-acne compound, an antioxidant, a sunscreen agent, a vitamin, retinol, a retinoid, an anti-inflammatory, an analgesic, or an antibiotic, or any combination of these.

In other implementations, the bisabolol of the composition of bakuchiol and bisabolol is substituted with at least one of benzoyl peroxide, tretinoin, retinol, tazarotene, or an antibiotic, or a combination of these. For example, in a specific implementation, the composition includes bakuchiol, salicylic acid, and at least one of benzoyl peroxide, tretinoin, retinol, tazarotene, or an antibiotic.

In other implementations of the composition, the bakuchiol of the composition of bakuchiol and bisabolol is substituted with at least one of benzoyl peroxide, tretinoin, retinol, tazarotene, or an antibiotic, or a combination of these. For example, in a specific implementation, the composition can include bisabolol, salicylic acid, and at least one of benzoyl peroxide, tretinoin, retinol, tazarotene, or an antibiotic.

The composition in these implementations is not limited to the specific ingredients presented. A composition may have additional compounds (not necessarily described in this application), different compounds which replace some of the compounds presented, fewer of the compounds presented, or any combination of these. For example, Bakutrol and bisabolol can be combined with other active ingredients (not presented above) such as benzoyl peroxide, retinoids (e.g., retinol and tretinoin), and antibiotics (e.g., erythromycin and clindamycin), and the remainder is an emollient, water and other solvents. In these implementations, various ingredients other than those presented above can be used in combination with bakuchiol (e.g., other solvents such as caprylyl glycol, ethylhexylglycerin, PPG-2 isoceteth-20 acetate, and others).

Table A below provides the range of amount (percentage by weight) of each ingredient that can be used, while still maintaining its efficacy as an acne treatment agent. In the ingredient column, a trade name (in parentheses) for a product having the ingredients listed is also given. It should be understood that the invention is not limited to the specific percentages presented. A formulation of the invention may have additional compounds (not necessarily described in this application), different compounds which replace some of the compounds presented, fewer of the compounds presented, or any combination of these. Further, the compounds in other implementations of the invention may not be exactly the same as the compounds presented and may be modified or altered as appropriate for a particular application or based on the data or situation. For example, the percentages can also be specified by volume.

TABLE A

| Item Number | Ingredient | Range (Percentage by Weight (% WT/WT)) |
|---|---|---|
| 1 | Deionized Water | 40.00-80.00 |
| 2 | Hydroxyethylcellulose, Sodium Nitrate, Water (Natrosol 250 HHX Pharm) | 0.10-5.00 |
| 3 | Disodium EDTA (Dissolvine Na2-P) | 0.01-1.00 |
| 4 | Sodium PCA, Water (Nalidone) | 0.10-5.00 |
| 5 | Butylene Glycol (1,3-Butylene Glycol) | 0.10-5.00 |
| 6 | Salicylic Acid (Curcylic SA 100) | 0.10-5.00 |
| 7 | Glycolic Acid, Water (Glypure 70) | 10.00-20.00 |
| 8 | Lactic Acid, Water (Purac HiPure 90) | 0.10-5.00 |
| 9 | Deionized Water | 5.00-15.00 |
| 10 | Sodium Hydroxide (Sodium Hydroxide, Pellets, NF) | 1.00-5.00 |
| 11 | Deionized Water | 0.10-5.00 |
| 12 | Dextrin, *Perilla Ocymoides* Leaf extract (Shiso Extract Powder) | 0.01-1.00 |
| 13 | Deionized Water | 0.10-5.00 |
| 14 | *Olea Europaea* Fruit Extract, Water (Eurol BT) | 0.01-1.00 |
| 15 | Gluconolactone, Sodium Benzoate (Geogard Ultra) | 0.10-5.00 |
| 16 | Polysorbate 20 (Tween-20-LQ-(AP)) | 1.00-5.00 |
| 17 | Hydrolyzed *Psoralea Corylifolia* Extract (bakuchiol or Bakutrol ™) | 0.01-1.00 |
| 18A | Bisabolol (Bisabolol RAC) | 0.01-1.00 |
| 18B | Caprylyl Glycol (Lexgard O) | 0.01-1.00 |
| 18C | Ethylhexylglycerin (Sensiva SC 50) | 0.01-1.00 |
| 18D | PPG-2 Isoceteth-20 Acetate (CUPL PIC) | 0.10-3.00 |
| 19 | Encapsulated retinol | 0.05-5.00 |

In specific implementations, a composition for an acne solution includes 0.01 percent to about 1 percent by weight of bakuchiol, and about 0.01 percent to about 1 percent by weight of bisabolol RAC. In a specific implementation, the ratio of bakuchiol to bisabolol RAC is about 12:1, 12.8:1 11:1, 11.5:1, 10:1, 10.1:1, 10.2:1 10.5:1, 10.8:1 9:1, 9.5:1, 9.7:1, 9.8:1, 9.9:1, 8:1, 8.25:1, or 8.5:1. In other implementations, this ratio can vary. The composition can include a greater amount of bisabolol than of bakuchiol. In these implementations, the ratio can be about 1:1, 1:2, 1:4, 1:6, 1:8, or 1:10.

The ratios of bisabolol to bakuchiol can vary in different formulas based on the solubility of bakuchiol in each of the formulas. For example, one implementation of the formula can include bisabolol, bakuchiol, polysorbate 20, and salicylic acid. Another implementation of the formula can include bisabolol, bakuchiol, polysorbate 20, and benzoyl peroxide. The solubility of bakuchiol can be less in the formula with salicylic acid compared to the formula with benzoyl peroxide because bakuchiol is less able to solubilize with salicylic acid.

Furthermore, varying concentrations of ingredients (active or inactive ingredients) in formulas can change the solubility of bakuchiol in the formulas, thereby changing the ratios of bisabolol to bakuchiol. For example, one implementation of the formula can include bisabolol, bakuchiol, polysorbate 20, and 0.5 percent salicylic acid. Another implementation of the formula can include bisabolol, bakuchiol, polysorbate 20, and 1 percent salicylic acid. Bakuchiol's solubility in the formula with 0.5 percent salicylic acid can be different from its solubility in the formula with 1 percent salicylic acid. And the different solubility can affect the ratio of bisabolol to bakuchiol.

Furthermore, the ratios of bisabolol to bakuchiol can vary from a gel formula to a cleanser formula. As discussed above, the reason for the different ratios can be due to different active or inactive ingredients that are present in a gel formula and not present in a cleanser formula, or due to ingredients that are present in a cleanser formula and not present in a gel formula. Or a gel formula can contain the same ingredients as the cleanser formula, but in different concentrations. The different concentrations can result in different ratios of bisabolol to bakuchiol in a gel formula compared to a cleanser formula.

In a specific implementation, a composition includes about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight of bakuchiol. Additionally, the composition can include about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent of bisabolol RAC. Bakuchiol and bisabolol can be present in any combination of percentages, either individually or in combination.

Salicylic acid can be included in the composition in a range of about 0.10 percent to about 5.0 percent by weight. Salicylic acid is typically used to treat skin conditions including acne. The amount salicylic acid can vary in this range as appropriate for a particular application or based on the data or situation. In a specific implementation, the ratio of salicylic acid to bakuchiol is about 12:1, 12.8:1 11:1, 11.5:1, 10:1, 10.1:1, 10.2:1 10.5:1, 10.8:1 9:1, 9.5:1, 9.7:1, 9.8:1, 9.9:1, 8:1, 8.25:1, or 8.5:1. In other implementations, this ratio can vary. The composition can include a greater amount of bakuchiol than of salicylic acid. In these implementations, the ratio can be about 1:1, 1:2, 1:3, 1:4, 1:5, 1:6, 1:7, 1:8, 1:9 or 1:10. In a specific implementation, the composition includes about 0.5, 0.7, 0.75, 0.8, 0.85, 0.9, 0.95, 1.0, 1.05, 1.1, 1.15, 1.2, 1.25, 1.3, 1.35, 1.4, 1.5, 2.0, 2.5, 3.0, 4.0, or 5.0 percent by weight of salicylic acid. In an implementation, salicylic acid is present in an amount from about 0.5 percent to about 2 percent by weight (or equivalent amount by volume).

In a specific implementation, at least one of the ingredients presented in table A can be combined in any combination with benzoyl peroxide, tretinoin, retinol, tazarotene, or an antibiotic, or a combination of these. Some examples of antibiotics include clindamycin or erythromycin.

Benzoyl peroxide, tretinoin, retinol, tazarotene, or a hydrophobic antibiotic can be solubilized and developed into a formula similar to one listed in table A. In a specific implementation, a method to solubilize the above ingredients can include the same steps 1-9 in table B. In a step 10 (which is similar to step 10 of table B) of this implementation, benzoyl peroxide, tretinoin, retinol, tazarotene or a hydrophobic antibiotic can be premixed individually (not together in the same formula) with polysorbate 20 (item #16), bakuchiol (item #17), and bisabolol (item #18A) and mixed until uniform. Then the premix can be added to the first processing tank and mixed until completely uniform.

In a specific implementation, at least two of the following ingredients can be solubilized and developed into a formula similar to one listed in table A: benzoyl peroxide, tretinoin, retinol, tazarotene, or a hydrophobic antibiotic. In a specific implementation, a method to solubilize the above ingredients can include the same steps 1-9 in table B. In a step 10 (similar to step 10 of table B), the two or more ingredients to be solubilized can be premixed individually with polysorbate 20 (item #16), bakuchiol (item #17), and bisabolol (item #18A) and mixed until uniform. An example of premixing the ingredients individually with items #16, #17, and #18A is to premix the first ingredient with item #16, #17, and #18A and to premix the second ingredient with item #16, #17, and #18A, and so on for a third or fourth ingredient to be solubilized. Then the premixes can be added to the first processing tank and mixed until completely uniform.

In another implementation, least two of the following ingredients can be solubilized and developed into a formula similar to one listed in table A: benzoyl peroxide, tretinoin, retinol, tazarotene, or a hydrophobic antibiotic. In a specific implementation, a method to solubilize the above ingredients can include the same steps 1-9 depicted in table B. In a step 10, the ingredients to be solubilized can be combined together, then premixed with polysorbate 20 (item #16), bakuchiol (item #17), and bisabolol (item #18A), and mixed until uniform. Then the premix can be added to the first processing tank and mixed until completely uniform.

In an implementation, the composition can include about 2.5 percent to about 10 percent by weight (or equivalent amount by volume) of benzoyl peroxide. For example, in a specific implementation, the composition includes about 2.5, 3, 3.5, 4, 4.5, 5, 5.5, 6, 6.5, 7, 7.5, 8, 8.5, 9, 9.5, or 10 percent by weight. In another specific implementation, the composition includes 10 percent by weight or greater of benzoyl peroxide, for example, 10.1, 10.2, 10.3, 10.4, 10.5, 10.6, 10.7, 10.8, 10.9, 11, 12, 13, 14, or 15 percent or greater. In other implementations, the composition includes less than 2.5 percent by weight of benzoyl peroxide. For example, the composition includes 0.1, 0.5, 1, 1.5, 2.0, 2.1, 2.2, 2.3, or 2.4 percent or greater.

In an implementation, the composition can include about 0.025 percent to about 0.1 percent by weight (or equivalent amount by volume) of tretinoin. For example, in a specific implementation, the composition includes about 0.025, 0.05, 0.075, or 0.1 percent by weight. In another specific implementation, the composition includes 0.1 percent by weight or greater of tretinoin, for example, 0.125, 0.15, 0.175, or 0.2 percent or greater. In other implementations, the composition includes less than 0.025 percent by weight of tretinoin. For example, the composition includes about 0.02, 0.015, 0.01, 0.005, or 0.001 percent or less.

In an implementation, the composition can include about 0.1 percent by weight (or equivalent amount by volume) of tazarotene. In a specific implementation, the composition includes 0.1 percent by weight or greater of tazarotene, for example, 0.125, 0.15, 0.175, or 0.2 percent or greater. In other implementations, the composition includes less than 0.1 percent by weight of tazarotene. For example, the composition includes 0.09, 0.008, 0.07, 0.06, or 0.05 percent or less.

In an implementation, the composition can include about 1 percent to about 1.2 percent by weight (or equivalent amount by volume) of clindamycin. For example, in a specific implementation, the composition includes about 1, 1.05, 1.1, 1.15, or 1.2 percent by weight. In another specific implementation, the composition includes 1.2 percent by weight or greater of clindamycin, for example, 1.2, 1.25, 1.3, 1.35, 1.4, 1.45, or 1.5 percent or greater. In other implementations, the composition includes less than 1 percent by weight of clindamycin. For example, the composition includes about 0.9, 0.8, 0.7, 0.6, 0.5, 0.4, 0.3, 0.2, or 0.1 percent or less.

In an implementation, the composition can include about 2 percent to about 3 percent by weight (or equivalent amount by volume) of erythromycin. For example, in a specific implementation, the composition includes about 2, 2.1, 2.2, 2.3, 2.4, 2.5, 2.6, 2.7, 2.8, 2.9, or 3 percent by weight. In another specific implementation, the composition includes greater than about 3 percent of erythromycin, for example, 3, 3.1, 3.2, 3.3, 3.4, or 3.5 percent or greater. In other implementations, the composition includes less than 2 percent by weight of erythromycin. For example, the composition includes about 1.9, 1.8, 1.7, 1.6, 1.5, 1.4, 1.3, 1.2, 1.1, 1, or 0.5 percent or less.

In an implementation, the composition can include retinol. Retinol is a cosmetic ingredient and can be used in a wide range of concentrations. In a specific implementation, the amount of retinol in the composition can be from about 0.01 percent to about 20 percent. For example, the composition includes about 0.01, 0.1, 0.1, 0.5, 1, 1.5, 2, 2.5, 3, 3.5, 4, 4.5, 5, 10, 15, or 20 percent by weight. In another specific implementation, the composition includes 20 percent by weight or greater of retinol, for example, 21, 22, 23, 24, 25, 26, 27, 28, 29, or 30 percent or greater. In other implementations, the composition includes less than 0.01 percent by weight of retinol. For example, the composition includes about 0.009, 0.008, 0.007, 0.006, 0.005, 0.004, 0.003, 0.002, or 0.001 percent or less.

In a specific implementation, the composition includes alpha hydroxy acid (AHA). In implementations, alpha hydroxy acid can include one or more of glycolic acid, lactic acid, malic acid, citric acid, tartaric acid, or suitable mixtures of two or more thereof. In a specific implementation, the composition includes about 10 percent to about 20 percent of glycolic acid, and 0.10 percent to about 5 percent of lactic acid. For example, glycolic acid is present in about 10.5, 11.5, 12.5, 13, 13.5, 13.8, 14.0, 14.1, 14.3, 14.5, 14.8, 15.0, 15.3, 15.8, 16.0, 16.5, or 17.0 percent, and lactic acid is present in about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, or 4.0 percent. The amount of this combination of alpha hydroxy acids can be included individually or in combination.

The composition can include an extract derived from *Perilla Ocymoides* in an amount from about 0.01 to about 1.0 percent. For example, the amount of extract is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight. In a specific implementation the extract is an extract power from shiso.

The composition can also include an extract derived from the *Olea Europaea* fruit, in an amount from about 0.01 to about 1.0 percent. For example, the amount of extract is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight. The fruit is commonly called the olive.

The composition can include hydroxyethylcellulose in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, 4.0, 4.5, or 5.0 percent by weight.

Disodium EDTA can be included in an amount from about 0.01 to about 1 percent. For example, the amount of disodium EDTA is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight.

Sodium PCA can be included in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, 4.0, 4.5, or 5.0 percent by weight.

The composition can include butylene glycol in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight.

The composition can include sodium hydroxide in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight.

The composition can include sodium benzoate in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight. In a specific implementation, the composition includes sodium benzoate with gluconolactone.

The composition can include other ingredients including preservatives, thickeners, humectants, stabilizers, buffers, emollients, emulsifying agents, and water. In a specific implementation, the composition includes about 1 percent to about 5 percent by weight of polysorbate 20. For example, an amount of about 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight is included.

In other implementations, polysorbate 20 can be substituted with 0.01 percent to about 1 percent of caprylyl glycol. For example, an amount of about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight is included. In another specific implementation, caprylyl glycol can be substituted with 0.01 percent to about 1 percent of ethylhexylglycerin. For example, an amount of about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight is included. And in yet another specific implementation, ethylhexylglycerin can be substituted with 0.1 percent to about 3 percent of PPG-2 isoceteth-20 acetate. For example, an amount of about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, or 3.0 percent by weight is included. In these other implementations, other ingredients' weight by percentage can be adjusted accordingly. For example, in a composition using 1.00 percent PPG-2 isoceteth-20 acetate, an amount of deionized water can be increased or decreased accordingly.

The amount of water in the final composition can be from about 45 to about 99 percent. For example, in a specific implementation, deionized water is included in an amount of about 70, 70.5, 70.3, 70.9, 72.5, 72.9, 73.0, 73.1, 73.3, 73.4, 73.5, 73.6, 73.7, 73.9, 80.1, 80.15, 80.2, or 81.0 percent by weight.

The composition can be formulated as a water-based, topical gel. In a specific implementation, the gel is a semi-viscous gel solution. The solution can have a specific gravity from about 1.06 to 1.10, about 17.5 percent to about 21.5 percent of solids, a viscosity of about 4000 to about 8000 centipoise (cps), and a pH of about 3.5 to about 4.5.

Gels can be a solid three-dimensional network that spans the volume of a liquid medium and ensnares it through surface tension effects. This internal network structure may result from physical bonds (physical gels) or chemical bonds (chemical gels), as well as crystallites or other junctions that remain intact within the extending fluid. A gel vehicle with an aqueous nature can ensure that sebaceous follicles or pores do not get clogged with oils. Therefore, a water-based gel devoid of oils can be beneficial to skin.

The composition can also be formulated as a serum. A serum can be oil and water-based. A serum can be more difficult to apply onto the skin. However, a serum formulation can be desirable because a serum (compared to lotion, cream, and gel) is characterized by its rapid absorption, ability to penetrate into the deeper layers of the skin, nongreasy finish, and a formulation with a very high concentration of active substances (e.g., lipophilic compounds, anti-acne compounds, or retinoids, or antibiotics).

The composition can also be formulated as a lotion, which can be an oil-in-water emulsion or water-in-oil emulsion. Lotions can include fillers and emulsifiers to create a creamy lotion, and can introduce pore-clogging oils onto the skin. The oils, fillers, and emulsifiers can irritate and worsen acne. However, for users with dry skin and acne, such oils may not clog pores, and can instead improve acne by moisturizing and soothing dry skin.

The composition can be included in a cleanser, cream, lotion, serum, essence, balm, sunscreen, gel, or an emulsion (e.g., an oil-in-water emulsion or a water-in-oil emulsion). For example, the composition can be included in a group of products (e.g., day cream, night cream, cleanser, toner, and acne gel), prescribed for use together, in order to maximize the acne treatment properties of the composition. The composition can be alcohol-free or substantially alcohol-free. Formulations can include more or less humectants, oils, botanicals, or other ingredients where the composition is adjusted for different skin types (e.g., dry, oily, acne prone, combination, dull, sensitive, or aging skin).

A method of preparation includes a water-based acne gel composition. The preparation solubilizes bakuchiol (e.g. Bakutrol) and allows it to be stable in the gel.

A problem is bakuchiol (e.g., 60 percent of hydrolyzed *psoralea corylifolia* extract, such as found in Envy Medical's ClarityMD Cleanser and Gel) and bisabolol are very insoluble in water. Both bisabolol and bakuchiol are typically formulated into the oil phase of emulsions, per the ingredient manufacturers. However, the hydrolyzed *psoralea corylifolia* extract (60 percent bakuchiol) will not stay in solution and precipitates out when added to the oil phase of an emulsion. This prevents the hydrolyzed *psoralea corylifolia* extract from being absorbed by the pores of the skin. A more stable formula can be achieved if alcohol is added to the formula, but the alcohol is undesirable as it will irritate inflammatory acne lesions.

Therefore, what is needed is a method to formulate bakuchiol and bisabolol into an acne cleanser formula, including over 50 percent water, and into an acne gel formula including 60 percent water without the use of alcohol.

In an implementation, an acne cleanser formula can include less than 50 percent water. And in an implementation, an acne gel formula can include less than 60 percent water. An acne cleanser formula including less than 50 percent water or an acne gel formula including less than 60 percent water can result in a more anhydrous formula composed mostly of oil or silicone, which would not be ideal for application onto acneic skin. However, a more anhydrous formula with oils or silicone can be moisturizing and soothing for people with dry skin and acne.

In an implementation, an acne cleanser formula can include more than 50 percent water. And in an implementation, an acne gel formula can include more than 60 percent water. In a more specific implementation, an acne cleanser can include 55-65 percent water. In another specific implementation, an acne gel formula can include more than 70-75 percent water. Since anti-acne ingredients are typically hydrophobic, the concentration of water may not impact effectiveness of the cleanser or gel in addressing acne.

A method is used to obtain a formulation of an acne cleanser. In a specific implementation, the method includes premixing hydrolyzed *psoralea corylifolia* extract with alpha-bisabolol, Eurol BT, *olea europaea* (olive) fruit extract, phenoxyethanol, caprylyl glycol, hexylene glycol, ethylhexylglycerine, cocamidopropyl betaine, and sodium chloride, and then adding this mixture to the cleanser formula. The method yields a stable formula whereby the hydrolyzed *psoralea corylifolia* extract is completely solubilized.

A method is used to obtain a formulation of an acne gel. In a specific implementation, the method includes premixing hydrolyzed *psoralea corylifolia* extract with polysorbate 20 and bisabolol and then adding this mixture to the gel formula. The method yields a stable formula whereby the hydrolyzed *psoralea corylifolia* extract is completely solubilized.

By fully solubilizing the hydrolyzed *psoralea corylifolia* extract, the acne fighting ability of salicylic acid is enhanced because the particles of the ingredients can be readily absorbed by the skin. In both the acne cleanser and acne gel, this enhanced effect was substantiated by a clinical study that showed a 59 percent reduction in inflammatory acne lesions in just 7 days and over 90 percent reduction in 14 days. This is about two to three times faster reduction in acne lesions compared to the leading over-the-counter acne products on the market today.

The procedure listed below in table B provides a specific example of a preparation of a water-based acne gel including solubilized bakuchiol. The item numbers presented in table B are the item numbers as presented in table A above. The amount of each item is according to the ranges presented in table A, and in the specific implementations provided above. It should be understood that the invention is not limited to the specific percentages presented. A formulation of the invention may have additional compounds (not necessarily described in this application), different compounds which replace some of the compounds presented, fewer of the compounds presented, or any combination of these. Further, the compounds in other implementations of the invention may not be exactly the same as the compounds presented and may be modified or altered as appropriate for a particular application or based on the data or situation. For example, the percentages can also be specified by volume.

It should further be understood that the invention is not limited to the specific steps presented below. A preparation of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

One of ordinary skill in the art can recognize that the mixing time until uniformity of concentration in mixtures is achieved can vary from batch to batch. Mixing time can depend on batch size, batch temperature, type of mixing used by the manufacturing kettle, size of the manufacturing kettle, and model of the manufacturing kettle used.

Larger batches can require longer mixing times to achieve uniformity of concentration in mixtures. For example, for a small lab batch, after about one to five minutes, one can begin visual inspection for signs of uniformity. For a larger batch (e.g., large commercial production batch), one can wait for fifteen to twenty minutes before starting to visually check for signs of uniformity. Visual signs of uniformity can be a lack of lumps in the mixture, a smooth and even texture throughout the mixture, a uniform color throughout the mixture, and other signs. Signs of uniformity can be checked using machines (e.g., sensors) as well.

A batch at a higher temperature may achieve uniformity faster than a same-sized batch at a lower temperature. One of ordinary skill in the art would recognize that particles tend to move faster at a higher temperature. The faster movements shorten mixing time.

A manufacturing kettle (or a process kettle) can have different shapes of propellers for mixing. The propeller shapes can affect how fast uniformity can be achieved.

A manufacturing kettle can also have different speed settings for the propellers. For example, a higher speed would help a mixture achieve uniformity faster. A lower propeller speed can be from 30-60 revolutions per minute (rpm). A higher propeller speed can be from 900-3600 revolutions per minute. Mixing at higher propeller speed would shorten the amount of time for a mixture to achieve uniformity.

The size of manufacturing kettle can also affect the length of mixing time for a mixture to achieve uniformity. A larger sized manufacturing kettle can hold a larger batch of product or mixture. And as discussed above, a larger batch can achieve uniformity slower than a smaller batch.

The model of manufacturing kettle used can also affect the length of time for a mixture to achieve uniformity. One model of manufacturing kettle can have a round shape. Another model of manufacturing kettle can have a longer oval shape. The different shapes can affect how different layers of fluid flows within the mixture interact with each other (e.g., laminar flow or turbulent flow), which could affect the mixture's speed in achieving uniformity of concentration.

One of ordinary skill in the art can recognize that cooling rates of mixtures can also vary from batch to batch because they depend on the size of the production batch, the manufacturing kettle used, and other equipment factors. A larger batch can require a longer time to cool down. Manufacturing kettles can have different cooling methods built in, such as transferring heat of mixture into cooling water flows. Cooling rates can depend on the manufacturing kettle's capability in cooling a mixture. The batch can be mixed inside equipment made of material that is insulating or conductive. Cooling rate can be faster for equipment made of conductive material. And cooling rate can be slower for equipment made of insulating material.

Further, in the implementation shown in table B, temperatures are maintained, as directed, for each manufacturing step in approximately real time. The temperatures can be maintained using a steam jacket built into the manufacturing kettle.

Further, in the implementation shown in table B, the formula is constantly mixed throughout the entire manufacturing process until the production batch meets the formula specifications and is deemed completed. In other implementations, the formula may not be constantly mixed. For example, the procedure can be paused at a certain step, so that mixing is paused and the batch is be put away to be continued on another day.

TABLE B

| Phase | Step Number | |
|---|---|---|
| A | 1 | Into a first processing tank, equipped with a propeller mixer and side sweep, add item #1 (deionized water), which is at room temperature (about 20-26 degrees Celsius). Begin high speed mixing. Sprinkle in item #2 to the first processing tank. Mix for a sufficient time until completely uniform and free of lumps. This is a first mixture. Heat first mixture to 70-75 degrees Celsius. Add item #3 and item #4 to the first processing tank and mix, while maintaining the temperature at 70-75 degrees Celsius. This is a second mixture. Then cool the second mixture to 60-65 degrees Celsius while concurrently mixing. |
| B | 2 | In a second processing vessel or tank, add item #5 and item #6 at room temperature. This is a third mixture. Heat the third mixture to 60-65 degrees Celsius while mixing until the third mixture is uniform. Add the third mixture to the first processing tank. The first processing tank now contains a fourth mixture including the second and third mixture. Mix the fourth mixture for a sufficient time until completely uniform. After fourth mixture is uniform, cool to 55-60 degrees Celsius while concurrently mixing. |
| C | 3 | Add item #7 and item #8 to the first processing tank. Mix for a sufficient time until uniform while maintaining a temperature of 55-60 degrees Celsius. The first processing tank now contains a fifth mixture. After the fifth mixture is uniform, cool the fifth mixture to 50-55 degrees Celsius while concurrently mixing. |
| D | 4 | In a third processing vessel or tank, premix item #9 and item #10 for a sufficient time until item #10 is completely dissolved in item #9 at room temperature. A mix of item #9 and item #10 is a sixth mixture. Slowly add the sixth mixture to the first processing tank. Mix for a sufficient time until uniform, thereby obtaining a seventh mixture. After the seventh mixture is uniform, cool to 45-50 degrees Celsius while concurrently mixing. |
| E | 5 | In a fourth processing vessel or tank, premix item #11 and item #12 at room temperature, thereby obtaining an eighth mixture. Add the eighth mixture to the first processing tank. Mix for a sufficient time until uniform while maintaining a temperature of 45-50 degrees Celsius, thereby obtaining a ninth mixture. |
| F | 6 | In a fifth processing vessel or tank, premix item #13 and item #14 at room temperature, thereby obtaining a tenth mixture. Add the tenth mixture to the first processing tank. Mix for a sufficient time until uniform while maintaining a temperature of 45-50 degrees, thereby obtaining an eleventh mixture. After the eleventh mixture is uniform, cool to 40-45 degrees Celsius. |
| G | 7 | Add item #15 to the first processing tank. Mix for a sufficient time until uniform while maintaining a temperature of 40-45 degrees Celsius, thereby obtaining a twelfth mixture. |
| H | 8 | In a sixth processing vessel or tank, premix item #16, item #17, and item #18A at room temperature, thereby obtaining a thirteenth mixture. Add to the first processing tank. Mix for a sufficient time until completely uniform while maintaining a temperature of 40-45 degrees Celsius, thereby obtaining a fourteenth mixture. |
| | 9 | Add item #19 to the first processing tank. Mix for a sufficient time until uniform while maintaining a temperature of 40-45 degrees Celsius, thereby obtaining a fifteenth mixture. |
| | 10 | QS batch with deionized water if necessary. Continue mixing and cooling to 35 degrees Celsius. |

Referring to step 8, the fourteenth mixture is an aqueous mixture that is a combination of the twelfth and thirteenth mixtures. The fourteenth mixture is a water-based mixture that is a combination of the twelfth and thirteenth mixtures, and the fourteenth mixture does not include an oil constituent. In another specific implementation, the fourteenth mixture is a water-based mixture that is a combination of the twelfth and thirteenth mixtures, and the fourteenth mixture does not include an alcohol constituent. As discussed above, oil and alcohol are avoided because they can be skin irritants, which in an acne formulation can make an acne condition worse instead of better.

In a specific implementation, in step 8, the thirteenth mixture is added to the twelfth mixture (which is inside the first processing tank) at a temperature of less than 40 degrees Celsius to obtain a fourteenth mixture. The fourteenth mixture includes the solubilized hydrolyzed *psoralea corylifolia* extract. Thus, hydrolyzed *psoralea corylifolia* extract, bisabolol, and polysorbate 20 are solubilized at less than about 40 degrees, which is a lower temperature such as 75 degrees. Solubilizing at a lower temperature provides benefits. Using a lower temperature allows the particle size of bakuchiol in the hydrolyzed *psoralea corylifolia* extract to be smaller sized. More specifically, the lower temperature allows the particle size of bakuchiol in the hydrolyzed *psoralea corylifolia* extract to be of sufficiently small size to penetrate skin pores into sebaceous follicles where the hydrolyzed *psoralea corylifolia* extract can exert its antimicrobial and anti-inflammatory properties.

In step 9, item #19 is added to the fourteenth mixture (which is inside the first processing tank) at a temperature of less than 40 degrees Celsius to obtain a fifteenth mixture. The fifteenth mixture includes the solubilized hydrolyzed *psoralea corylifolia* extract, bisabolol, and encapsulated retinol. The combination of retinol and bakuchiol has an improved or synergistic effect on the efficacy in treatment of acne (compared to retinol by itself or bakuchiol by itself). The combination is as effective as tretinoin, which is available by prescription.

In a mixture including bakuchiol, bisabolol, and retinol, retinol does not need to be solubilized with bakuchiol because encapsulated retinol is added to the mixture. A reason is that the capsule of the encapsulated retinol can provide a shield a shield between retinol and bakuchiol and can decrease effects of (unencapsulated) retinol on the ability of bisabolol to solubilize bakuchiol. With less interaction between retinol and bakuchiol, retinol does not need to be solubilized with bakuchiol. And because encapsulated retinol does not need to be solubilized with bakuchiol, retinol can be added to separately to the mixture, after bakuchiol has been solubilized with bisabolol.

However, in an alternate implementation, instead of using an encapsulated retinol and unencapsulated retinol can be used to obtain an effective mixture including bakuchiol, bisabolol, and retinol. When using unencapsulated retinol, the unencapsulated retinol is solubilized with along with the bakuchiol and bisabolol (step 8 above).

In another specific implementation, in step 10, item 16 (polysorbate 20) can be substituted with an amount of caprylyl glycol (item #18B), while the other steps and ingredients are the same as presented in table B. In another specific implementation, in step 10, caprylyl glycol can be substituted with an amount of ethylhexylglycerin (item #18C). And in yet another specific implementation, in step 10, ethylhexylglycerin can be substituted with an amount of PPG-2 isoceteth-20 acetate (item #18D). In these other implementations, other ingredients' weight by percentage can be adjusted accordingly. For example, in a composition using 1.0 percent PPG-2 isoceteth-20 acetate, an amount of deionized water can be decreased or increased accordingly.

Table C below provides another implementation for an acne cleanser formulation. The of amounts (percentage by weight) of each ingredient are listed, while still maintaining its efficacy as an acne treatment agent (cleanser formulation), similar to table A.

TABLE C

| Item Number | Ingredient | Range (Percentage by Weight (% WT/WT)) |
|---|---|---|
| 1 | Deionized Water | 40.00-80.00 |
| 2 | *Aloe Barbadensis* Leaf Juice (Activera 1-200 C) | 0.10-5.00 |
| 3 | Glycerin, Water (Glycerine 99.7% USP) | 0.01-1.00 |
| 4 | Xanthan Gum (Keltrol CG) | 0.10-5.00 |
| 5 | Water, Decyl Glucoside (Plantaren 2000N UP) | 10.00-40.00 |
| 6 | Water, Cocamidopropyl Betaine, Sodium Chloride (Caltaine C-35) | 5.00-20.00 |
| 7 | Salicylic Acid (Curcylic SA 100) | 0.50-2.00 |
| 8 | Deionized Water | 0.10-5.00 |
| 9 | Sodium Hydroxide (Sodium Hydroxide, Pellets, NF) | 0.01-5.00 |
| 10 | Deionized Water | 1.00-5.00 |
| 11 | *Sapindus Mukurossi* Peel Extract (Barcleanse NL) | 0.01-5.00 |
| 12 | Dipotassium Glycyrrhizate (ARG-DPG) | 0.01-5.00 |
| 13 | Dextrin, *Perilla Ocymoides* Leaf extract (Shiso Extract Powder) | 0.01-2.00 |
| 14 | Bisabolol (Alpha-Bisabolol, Natural) | 0.05-2.00 |
| 15 | Hydrolyzed *Psoralea Corylifolia* Extract (bakuchiol or Bakutrol(TM)) | 0.05-2.00 |
| 16 | *Olea Europaea* Fruit Extract, Water (Eurol BT) | 0.05-5.00 |
| 17 | Phenoxyethanol, Caprylyl Glycol, Hexylene Glycol, Ethylhexylglycerin (Botanistat PF-64) | 0.05-5.00 |
| 18 | Water, Cocamidopropyl Betaine, Sodium Chloride (Caltaine C-35) | 0.10-5.00 |

In an implementation, *Aloe barbadensis* leaf juice is used as a skin conditioner or moisturizer. *Aloe barbadensis* can be substituted with other forms of aloe, such as Aloe barnadensis leaf juice powder or extract. *Aloe barbadensis* can be substituted with a similar performing skin conditioner using a one to one ratio. *Aloe barbadensis* can be substituted with other skin conditioners using a ratio (*Aloe barbadensis* to substitute) of 0.01:1, 0.1:1, 0.5:1, 1:1, 2:1, 3:1, 5:1, 10:1, or more. In another implementation, the mixture does not contain a skin conditioner. In another implementation, *Aloe barbadensis* can be immaterial to the performance of the formula.

Xanthan gum can be a gel forming (or viscosity controlling) agent. In another implementation, Xanthan gum can be substituted with a similar performing gel forming agent (e.g., Carbopol® 941 and others) using a ratio (Xanthan gum to substitute) of 0.01:1, 0.1:1, 0.5:1, 1:1, 2:1, 3:1, 5:1, 10:1, or more. In another implementation, the mixture does not contain a viscosity controlling agent.

Decyl glucoside can be used as a surfactant, or a skin cleansing agent, or a combination of both. Decyl glucoside can be substituted with a surfactant (e.g., polysorbate 20 or other surfactants previously mentioned) or with a skin cleansing agent, or with a combination of both surfactant and skin cleansing agent, using a ratio (decyl glucoside to surfactant substitute or decyl glucoside to skin cleansing agent substitute) of 0.01:1, 0.1:1, 0.5:1, 1:1, 2:1, 3:1, 5:1, 10:1, or more.

More than one type of surfactant can be used. For example, decyl glucoside and cocamidopropyl betaine can be combined in a single formula. In specific implementations, decyl glucoside and cocamidopropyl betaine can be combined in ratios (decyl glucoside to cocamidopropyl betaine) of 1:1, 1.55:1, 1.87:1, 1.94:1, 1.95:1, 2.01:1, 2.05:1, 2.07:1, 2.08:1, 2.09:1 2.11:1, 3.09:1, 4.0:1, 1:4, 1:3, 1:2.5, 1:2, 1:1.5, 1:1.05, and more.

A list of substitutes for surfactants and skin cleansing agents can be found at Paula's Choice skin care Web site: http://www.paulaschoice.com/cosmetic-ingredient-dictionary/surfactants-detergent-cleansing-agents, which is incorporated by reference.

In an implementation, *sapindus mukurossi* peel extract can be used as a skin conditioning agent, or an anti-irritant, or a combination of both. *Sapindus mukurossi* peel extract can be substituted with a skin conditioning agent or with an anti-irritant, or with a combination of both (e.g., dipotassium glycyrrhizate and others), using a ratio (*sapindus mukurossie* peel extract to skin conditioning agent substitute or *sapindus mukurossie* peel extract to anti-irritant substitute) of 0.01:1, 0.1:1, 0.5:1, 1:1, 2:1, 3:1, 5:1, 10:1, or more. A list of substitutes for skin conditioning agents and anti-irritants can be found at Paula's Choice skin care Web site: http://www.paulaschoice.com/cosmetic-ingredient-dictionary/anti-irritants, which is incorporated by reference.

In another implementation, more than one type of skin conditioning agent or anti-irritant can be used. For example, *sapindus mukurossi* peel extract and dipotassium glycyrrhizate can be combined in a single formula. In specific implementations, *sapindus mukurossi* peel extract and dipotassium glycyrrhizate can be combined in ratios (*sapindus mukurossi* peel extract to dipotassium glycyrrhizate) of 1:1, 1.5:1, 2:1, 3:1, 5:1, 10:1, 1:1.5, 1:2, 1:3, 1:5, 1:10, and more.

The procedure listed below in table D provides another specific example of preparing a mixture for an acne cleanser including solubilized bakuchiol, similar to table B. The item numbers presented in table D are the item numbers as presented in table C above. The amount of each item is according to the ranges presented in table C. It should be understood that the invention is not limited to the specific percentages presented in table C.

TABLE D

| Phase | Step Number | |
|---|---|---|
| A | 1 | Into a first processing tank, equipped with a propeller mixer and side sweep, add item #1 (deionized water). Item #1 is at room temperature (about 20-26 degrees Celsius). Begin high speed mixing. Heat item #1 to about 70-75 degrees Celsius. Sprinkle in item #2. Mix item #1 and item #2 for a sufficient amount of time until completely uniform and free of lumps. Maintain temperature at about 75 degrees Celsius. |
| B | 2 | In a second processing vessel or tank, premix item #3 and item #4 at room temperature. Mix item #3 and item #4 for a sufficient amount of time until uniform. Add mixture of item #3 and item #4 to first processing tank. Mix until uniform while maintaining the temperature at 70-75 degrees Celsius. |
| C | 3 | Add item #5 to the first processing tank. Mix mixture inside the first processing tank for a sufficient amount of time until uniform while maintaining temperature at 70-75 degrees Celsius. Then cool mixture inside the first processing tank to 60-65 degrees Celsius while concurrently mixing. |
| D | 4 | In a third processing vessel or tank, premix item #6 and item #7. Heat mixture inside third processing vessel or tank to about 60-65 degrees Celsius while concurrently mixing. Mix for a sufficient amount of time until mixture in third processing vessel or tank is uniform. Add mixture in third processing vessel or tank to the first processing tank. Mix mixture inside first processing tank for a sufficient amount of time until completely uniform while maintaining a temperature of 60-65 degrees Celsius. |
| E | 5 | In a fourth processing vessel or tank, premix item #8 and item #9 at room temperature (about 20-26 degrees Celsius) until item #9 is completely dissolved in item #8. Add mixture inside the fourth processing vessel and tank to the first processing tank. Mix mixture inside the first processing tank for a sufficient time until uniform while maintaining a temperature of 60-65 degrees. Then cool mixture inside first processing tank to about 50-55 degrees Celsius while concurrently mixing. |
| F | 6 | In a fifth processing vessel or tank, add items #10 to #13 at room temperature. Mix mixture inside fifth processing vessel or tank for a sufficient time until uniform. Add mixture inside fifth processing tank to the first processing tank. Mix mixture inside first processing tank until uniform while maintaining a temperature of 50-55 degrees Celsius. |
| G | 7 | In a sixth processing vessel or tank, add items #14 to #18 at room temperature. Mix mixture inside sixth processing vessel or tank for a sufficient time until uniform. Add the mixture inside the sixth processing vessel or tank to the first processing tank. Mix mixture inside first processing tank for a sufficient time until uniform at a temperature of 50-55 degrees Celsius. Then cool mixture inside the first processing tank to 30-35 degrees Celsius. |
| | 8 | QS batch (in other words, quantum sufficit, or replace the water that has been lost to evaporation during the manufacturing process) with deionized water, if necessary. Continue mixing the mixture inside the first processing tank and cool down to room temperature. |
| | 9 | If a higher pH (or the negative log of a hydrogen ion concentration in an aqueous solution) of mixture is desired, add sodium hydroxide in increments until the desired pH is achieved. |

The above cleanser formulation can also include retinol, as the gel, lotion, or similar formulation in tables A and B. An encapsulated retinol can be mixed with the above mixture after step 7. For unencapsulated retinol, the unencapsulated retinol can be solubilized along with the bakuchiol and bisabolol in step 6.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method of preparing an aqueous mixture comprising:
mixing deionized water and hydroxyethylcellulose to obtain a first mixture;
applying heat to the first mixture until the first mixture reaches about 75 degrees Celsius;
adding disodium ethylenediaminetetraacetic acid (EDTA) and sodium pyrrolidone carboxylic acid (PCA) to the first mixture and mixing to obtain a second mixture;
allowing the second mixture to cool to from about 60 to 65 degrees Celsius;

mixing butylene glycol and salicylic acid to obtain a third mixture;

applying heat to the third mixture until the third mixture reaches about 65 degrees Celsius;

mixing the third mixture and second mixture together to obtain a fourth mixture;

allowing the fourth mixture to cool to from about 55 to 60 degrees Celsius;

adding glycolic acid and lactic acid to the fourth mixture and mixing to obtain a fifth mixture;

allowing the fifth mixture to cool to from about 50 to 55 degrees Celsius;

mixing deionized water and sodium hydroxide to obtain a sixth mixture;

mixing the sixth mixture and the fifth mixture together to obtain a seventh mixture;

allowing the seventh mixture to cool to from about 45 to 50 degrees Celsius;

mixing deionized water and *perilla ocymoides* leaf extract to obtain an eighth mixture;

mixing the eighth mixture and the seventh mixture to obtain a ninth mixture;

mixing deionized water and *olea europaea* fruit extract to obtain a tenth mixture;

mixing the tenth mixture and ninth mixture to obtain an eleventh mixture;

allowing the eleventh mixture to cool to from about 40 to 45 degrees Celsius;

adding sodium benzoate to the eleventh mixture and mixing to obtain a twelfth mixture;

solubilizing an unsolubilized hydrolyzed *Psoralea corylifolia* extract to obtain a solubilized hydrolyzed *Psoralea corylifolia* extract comprising mixing the unsolubilized hydrolyzed *Psoralea corylifolia* extract, bisabolol, and polysorbate 20 to obtain a thirteenth mixture, and adding the thirteenth mixture to the twelfth mixture at a temperature of less than about 40 degrees Celsius to obtain a fourteenth mixture, wherein the fourteenth mixture comprises the solubilized hydrolyzed *Psoralea corylifolia* extract;

mixing encapsulated retinol to the fourteenth mixture to obtain a fifteenth mixture;

allowing the fifteenth mixture to cool to about 35 degrees Celsius; and obtaining an aqueous mixture that is a combination of the twelfth and thirteenth mixtures and retinol, wherein the aqueous mixture comprises an oil-free, water-based, anti-acne gel.

2. The method of claim 1 comprising:

adding benzoyl peroxide to the polysorbate 20, bisabolol, and hydrolyzed *Psoralea corylifolia* extract of the thirteenth mixture.

3. The method of claim 1 wherein the aqueous mixture comprises at least one of a retinoid or an antibiotic.

4. The method of claim 1 wherein the hydrolyzed *Psoralea corylifolia* extract comprises bakuchiol.

5. The method of claim 1 wherein the aqueous mixture does not comprise an alcohol constituent.

6. The method of claim 1 wherein the aqueous mixture does not comprise an oil constituent.

7. The method of claim 1 wherein the solubilizing an unsolubilized hydrolyzed *Psoralea corylifolia* at a temperature of less than about 40 degrees Celsius results in a particle size of bakuchiol in the hydrolyzed *Psoralea corylifolia* extract that is of a sufficiently small size to penetrate skin pores into sebaceous follicles where the hydrolyzed *Psoralea corylifolia* extract can exert its antimicrobial and anti-inflammatory properties.

\* \* \* \* \*